United States Patent [19]
Johnson

[11] 4,445,858
[45] May 1, 1984

[54] APPARATUS FOR PHOTO-CURING OF DENTAL RESTORATIVE MATERIALS

[75] Inventor: Clifford C. Johnson, Arlington Heights, Ill.

[73] Assignee: American Hospital Supply Corporation, Evanston, Ill.

[21] Appl. No.: 350,241

[22] Filed: Feb. 19, 1982

[51] Int. Cl.³ .............................................. A61C 3/00
[52] U.S. Cl. .................................... 433/141; 433/229
[58] Field of Search ..................... 350/96.24; 433/141, 433/229

[56] References Cited

U.S. PATENT DOCUMENTS

| | | | |
|---|---|---|---|
| 2,840,070 | 6/1958 | Tofflemire | 433/29 |
| 3,524,045 | 8/1970 | Siegel | 433/32 |
| 3,868,513 | 2/1975 | Gonser | 433/228 |

*Primary Examiner*—Robert Peshock
*Attorney, Agent, or Firm*—Tilton, Fallon, Lungmus

[57] ABSTRACT

An apparatus for use in curing dental restorative materials by means of visible (or ultraviolet) light. High intensity light is transmitted from a light box to the operative site by a fiber-optic cable and a hand-held light wand, the wand having a tip for directing the light towards the polymerizable material at the site of restoration. Proper spacing of the tip from the material to be cured is achieved by a conical shield which also functions to concentrate the light and to immobilize the hand-held wand in relation to the tooth undergoing restoration, without at the same time risking direct contact with and possible marring of the material to be photo-cured. A holder releasably supports the wand until use is required, the holder having a recess for receiving the shielded tip of the wand to protect the patient and others from the dazzling and discomforting effects of misdirected high-intensity light. The fiber-optic cable has its proximal end plugged into one of a plurality of sockets provided by the light box, the other sockets being adapted to receive the plugs of fiber-optic cables extending to other dental instruments capable of being illuminated by light from the same source.

20 Claims, 4 Drawing Figures

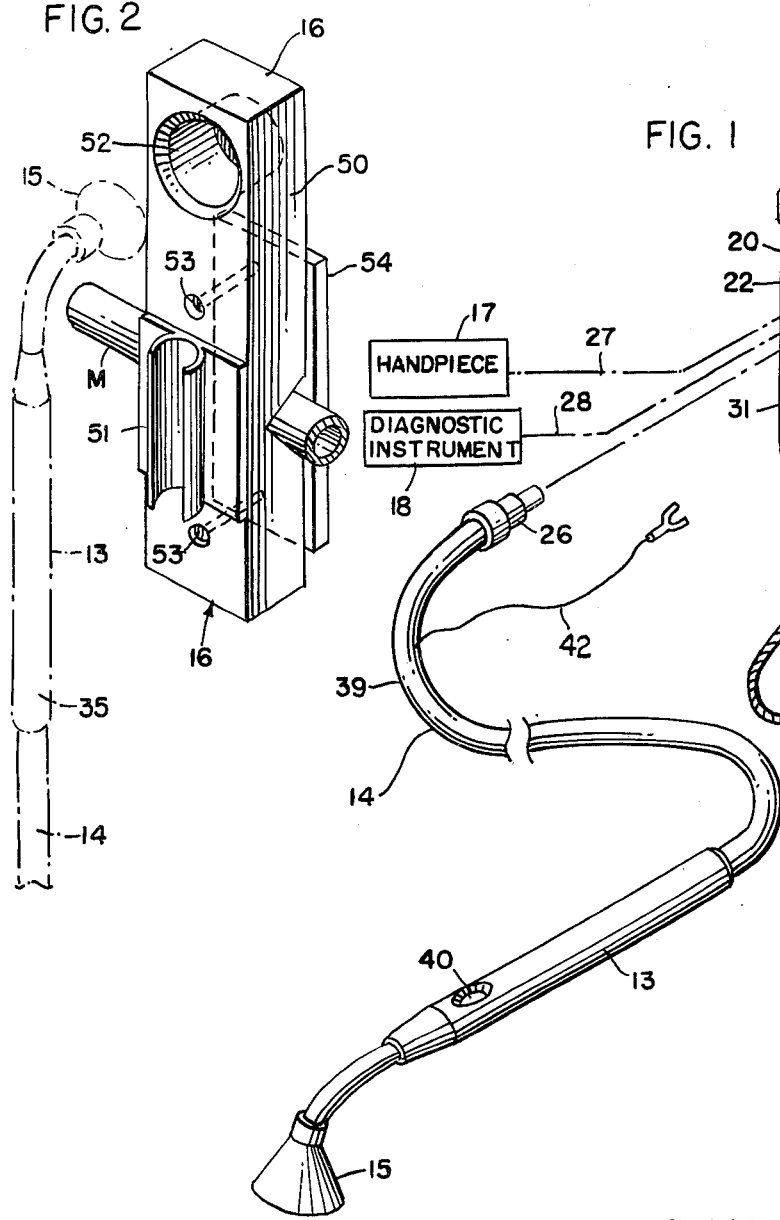
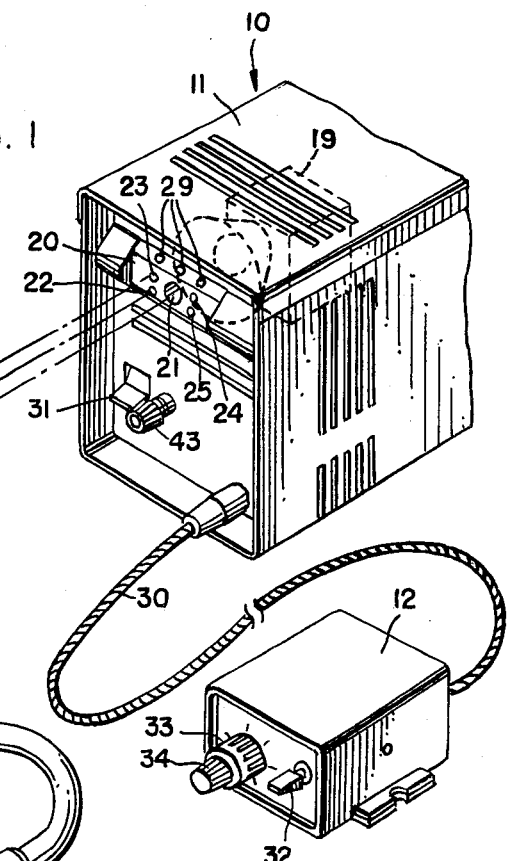
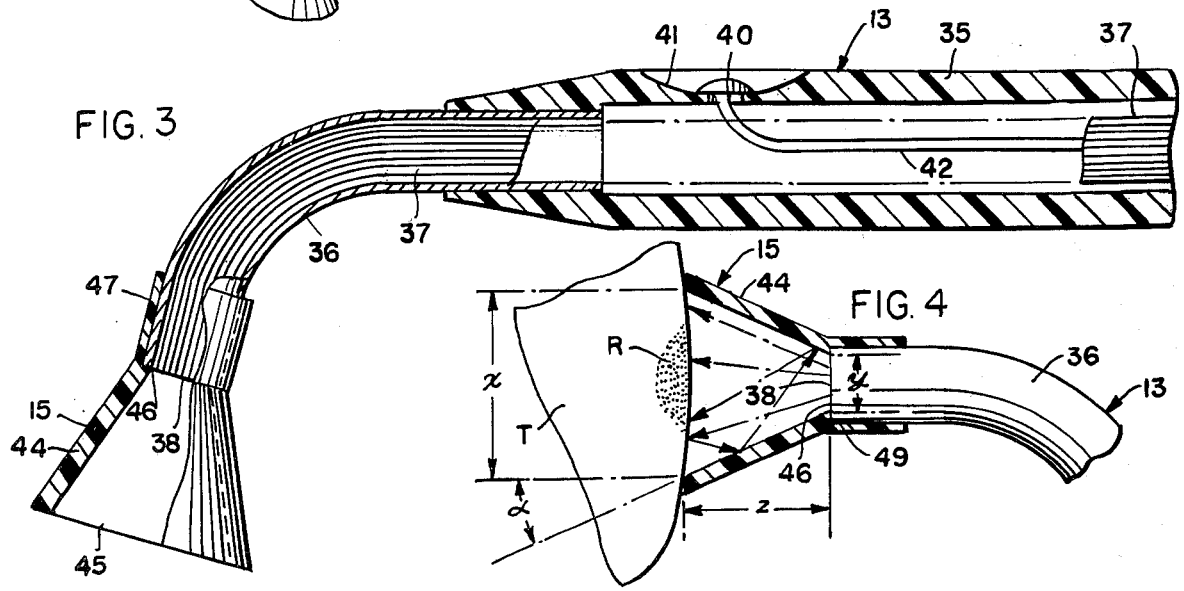

APPARATUS FOR PHOTO-CURING OF DENTAL RESTORATIVE MATERIALS

BACKGROUND AND SUMMARY

The use of polymerizable dental restorative materials capable of being cured by short-term (usually one minute or less) exposure to high-intensity light has become popular in recent years. Such a material allows a dentist all of the time needed to mold and shape the material in a prepared cavity or on a prepaved surface. Curing is commenced only when the dentist is satisfied with the results of the prior steps. The light may be of any suitable wavelength although preferably light in the visible spectrum is used, thereby avoiding the risks of exposure to light of shorter wavelengths (i.e., ultraviolet light.) After a few seconds of exposure to the high-intensity light, transmitted from the light source to a hand-held wand by means of a fiber-optic cable, the restoration is ready for final trimming and finishing.

Despite the advantages of such a system, it has been discovered that problems and disadvantages do exist. A conventional wand contains the distal end of the fiber-optic cable, the wand having a rigid tubular tip that supports the end of the cable and permits a dentist to direct the light to the area of restoration. Sufficiency of light exposure is critical for proper curing; consequently, conventional systems commonly include an electronic or mechanical timer which the dentist presets according to the manufacturer's instructions. (The duration of recommended exposure ordinarily varies with the shade and brand of the restorative material selected.) However, should the dentist hold the tip of the wand too far away from the area of restoration, inadequate curing may result. Should the tip be too close, the lighted area may not be large enough to cure the entire restoration, leaving marginal areas incompletely cured, or the tip may inadvertently contact the uncured restorative material, marring the prior work and possibly causing the restorative material to cling to, and subsequently harden upon, the tip of the wand.

Another problem in the use of conventional systems concerns the discomfort and temporary visual impairment that may result should the patient (or anyone else) look directly at the tip of the wand while it is illuminated. Even the dentist may be affected by direct or reflected light as he (she) looks directly at the restoration area during light-curing. In an effort to reduce such problems, some manufacturers provide filter caps that may be fitted over the tips of the wands to reduce the intensity of the light and thereby reduce eye discomfort and "after-image" effects; however, such filter caps also have the disadvantage of reducing the illuminating efficiency of such a system and increasing the light exposure time required for polymerization of the restorative materials.

A main object of this invention therefore lies in providing an improved apparatus which overcomes or at least greatly reduces the problems associated with conventional systems for photo-curing polymerizable dental restorative materials. Specifically, it is an object to provide a system in which means are provided for accurately controlling the distance between the tip of a wand and the area of restoration during a light-curing step, for intensifying the light directed to the restorative area during such a step, and for protecting the dentist against exposure to reflected light that might otherwise cause eye discomfort and after-image effects. It is a further object to provide such improvements while at the same time reducing the possibilities of direct contact between the tip of the wand and uncured material at the site of restoration that might mar the restoration and impair the usefulness of the instrument. In addition, the means for achieving such results also tends to protect the patient from visual exposure to light from the tip of the wand that might otherwise result in discomfort and temporary visual aberrations.

Briefly, the apparatus includes a light source, a light-directing wand adapted to be hand-held by the user (a dentist or dental assistant), a fiber-optic cable for transmitting light from the source to the wand, and a frusto-conical shield detachably connected to the tip of the wand. The shield has a collar portion extending from its reduced end, the collar being adapted to receive the tip portion of the wand. The shield is preferably opaque, or at least of low light transmissibility, and may be formed of relatively stiff polymeric material. The opening at the shield's enlarged end has a diameter falling generally within the range of 0.35 to 0.85 inches, the preferred range being approximately 0.40 to 0.65 inches. The angle of slope of the frusto-conical shield may fall within the general range of 15° to 35° (measured from the longitudinal axis of the shield), with a range of 20° to 25° being preferred.

A holder, adapted to be mounted near the dental tray or at any other convenient location, may be used to support the shielded wand when it is not in use but may nevertheless be illuminated, so that the risks a dentist or patient might be dazzled by the high-intensity light will be significantly reduced prior to or immediately following a light-curing operation. Efficiency is promoted by providing a light box having a plurality of sockets illuminated by a single light source, so that the same source is used to illuminate not only the light wand but also one or more other handpieces and/or diagnostic instruments.

Other features, objects, and advantages of the invention will become apparent from the specification and drawings.

DRAWINGS

FIG. 1 is a fragmentary and somewhat schematic perspective view illustrating an apparatus embodying this invention.

FIG. 2 is a perspective view showing the wand holder that may form a part of such apparatus, the wand being depicted in phantom to show its relationship to the holder.

FIG. 3 is an enlarged fragmentary longitudinal sectional view showing the distal end of a wand equipped with a replaceable frusto-conical light shield.

FIG. 4 is a somewhat schematic cross sectional view illustrating the apparatus in use, and certain of the important dimensional relationships of the frusto-conical shield.

DETAILED DESCRIPTION

Referring to the drawings, the numeral 10 generally designates a system or apparatus that includes light box 11, remote control unit 12, light wand 13, fiber-optic cable 14, spacer shield 15, and holder 16. One or more additional illuminated instruments may be included as part of the total system as represented schematically at 17 and 18 (FIG. 1).

Within box 11 is a high-intensity light source 19 that directs light towards a face plate 20 at the front of the box. For example, the light source may be a 250 watt, 120 volt A.C. tungsten-halogen lamp (Sylvania ENH or ETJ or equivalent). The face plate 20 has a plurality of sockets 21-25 for receiving the plugs or coupling elements of a plurality of illuminated instruments. Thus, the plug 26 at the proximal end of fiber-optic cable 14 is adapted to be received in central socket 21, and instruments 17, 18 may have light-transmitting cables 27, 28 provided with similar (but preferably smaller) plugs or coupling elements capable of being received within any of the sockets 22-25. All of the instruments, including wand 13, are therefore illuminated by the same high-intensity light source 19. The plugs received in sockets 23, 21, and 24 are anchored in place by set screws 29, and similar screws (not shown) may extend upwardly from beneath face plate 20 to secure plugs in sockets 22 and 25. Those sockets that are not used may, if desired, be closed off by any suitable closure means such as, for example, small plastic plugs or closure elements (not shown) adapted to be received within the unused sockets.

In accordance with conventional practice, light box 11 would normally be mounted on or within a dental console, or on the main column for a dental tray, in contrast to a more readily accessible location on or adjacent the tray itself, because frequent access to the relatively bulky light box is unnecessary. The more compact remote control unit may be mounted on, alongside, or beneath the tray or at some other convenient location within easy reach of the dentist or assistant. In accordance with standard practice, the remote control unit is connected to the main unit or light box 11 by power line 30. Switch 31 of the main unit is a master switch that would, following usual practice, be switched "on" at the beginning of each day to arm the system and activate a cooling fan within the light box. A three-position selector switch 32 is located at the control unit 12. When the lever of switch 32 is in the intermediate position shown, light source 19 is "off" (even though master switch 31 may be in an "on" position); when the selector switch 32 is raised, the system is in a light-cure operation mode, and when the switch is lowered, the system is in a handpiece operation mode. Concentric knobs 33 and 34 also project from remote control unit 12. Knob 33 is a selector knob for controlling the duration of illumination (between usual limits of about 2 to 60 seconds) during the light-cure operation mode, and knob 34 controls the intensity of illumination of light source 19 during the handpiece operation mode. When wand 13 is to be used, and switch 32 is raised into the light-cure operation mode, intensity control 34 is inoperative (the light source 19 automatically operates at maximum intensity) and timer control 33 is operative. Conversely, when selector switch is in its lowered position for handpiece operation, timer control 33 is inoperative. Since the essential structure and operation of the remote control unit 12 and its relationship to main unit 11 is conventional, the above description is set out for background purposes, and further discussion of such structure and operation are believed unnecessary herein.

Wand 13 includes a tubular handle 35 with a curved, rigid, tubular extension 36 projecting from the distal end of the handle. The fiber-optic bundle 37 of cable 14 extends through the handle and into tubular extension 36, terminating at the distal or tip end 38. The fiber bundle 37 extends back through cable 14 to plug 26 and socket 21. A conventional flexible protective sheath 39 extends about the bundle between plug 26 and wand 13, all as well known in the art. A metallic contact element 40 is mounted within an external recess 41 of handle 35 and is electrically connected by conductor 42 to binding post 43 of main unit 11. Finger contact with the button or contact element 40 activates light source 19 to cause light to be emitted from the tip or distal end 38 of the wand. Preferably, the system is wired so that the light will remain "on" as long as finger contact with button 40 is maintained. Removal of the finger from button 40 initiates operation of the timer, so that the light will continue to remain "on" for an additional interval determined by the selected setting of timer knob 33.

Referring to FIGS. 3 and 4, light shield 15, which also functions as a spacer element, is mounted at the distal end or tip of the wand. The shield includes a frusto-conical portion 44 having an enlarged end 45 and a reduced end 46, and an integral collar portion 47 continuing from the reduced end. The collar portion frictionally receives the tip end of the wand.

Certain dimensions and angular relationships of the shield are of particular importance since, in use, the shield functions to space the tip 38 of the wand from the surface of a tooth T as shown in FIG. 4. The internal diameter x of the shield at its enlarged end should fall within the general range of 0.35 to 0.85 inches, the preferred range being 0.40 to 0.65 inches. Particularly effective results have been obtained with an opening of a diameter of 0.50 inches. In addition, the slope $\alpha$ of the frusto-conical shield, measured from the longitudinal axis of the shield, should be within the range of 15° to 35°, the preferred range being 20° to 25°. An angle of 22° is shown in the drawings and has been found particularly effective.

Other dimensions, such as the internal diameter y at the reduced end of the shield, are less critical and would be determined primarily by the dimensions of the wand 13 upon which the shield is to be fitted. In general, the diameter y would ordinarily fall within the range of 0.15 to 0.30 inches. The length z of the frusto-conical portion 44 would generally fall within the range of 0.25 to 0.50 inches.

As shown most clearly in FIG. 4, the inside diameter of the cylindrical collar portion 47 is slightly larger than the opening 46 at the reduced end of frusto-conical portion 44, providing an internal annular shoulder 49 between the two portions that engages the end of the wand and effectively limits the extent to which the tip of the wand may be inserted into the shield. When the parts are fitted together, the tip or end surface 38 of the wand is therefore automatically located at the point of smallest internal diameter (i.e., opening 46) of frusto-conical portion 44.

The shield is formed of an opaque material, or at least a material having low light transmissivity, that is suitable for making direct contact with enamel and other oral surfaces. Relatively rigid polymeric materials, such as copolymers of acrylonitrile, butadiene, and styrene, or materials such as nylon or polypropylene, may be effectively used. The interior surface of the frusto-conical portion 44 should be reflective, either by reason of the composition and color of the material of the shield, or because of subsequent plating or coating of the interior surface. FIG. 4 schematically depicts the reflection and redirection of light rays that, in the absence of the shield, would tend to be reflected off of the tooth surface and away from the operative site. The redirection of the rays by the reflective inside surface of portion 44, back towards the area of restoration R, intensifies the light impinging on restoration R and promotes curing of the polymerizable material.

The photo-curing material may be any of a variety of dental composites commercially available for this purpose. While the formulas are proprietary, such materials are well known in the dental field as, for example, Durafill, available from Kulzer, Inc., Laguna Hills, Calif., Heliosit, from Vivadent (U.S.A.), Inc., Tonawanda, N.Y., Visar-Fil, from Den-Mat, Inc., Santa Maria, Calif., Estilux, from Kulzer, Inc., Laguna Hills, Calif., and Visio-Dispers, from ESPE, Norristown, Pa. Preferably, the restorative material is a composite capable of being polymerized by visible light, but restoratives that are capable of being cured with ultraviolet light may also be used and are included in this list (e.g., Estilux).

Prior to using the light-curing wand 13, the dentist prepares the tooth by cleaning and shaping the area for restoration, acid-etching the surface, and then applying in one or more steps the light-curable restorative material. Depending on the particular technique and brand of material used, the consistency of such material may vary from a liquid state (as where a polymerizable coating is applied to the cavity in advance of a moldable second material) to a semi-solid putty-like consistency. The final layer of restorative material is molded and smoothed by means of suitable dental instruments so that it matches the contour of the surrounding tooth, as indicated in FIG. 4. The light wand 13, equipped with the spacer shield 15, is then positioned as shown, with the edge of the shield about enlarged opening 45 engaging the tooth well beyond the margin of the soft uncured restorative material R. The conical shield thereby performs multiple functions. It spaces the light-emitting end surface 38 of the wand the optimum distance z from the area of restoration and provides a brace or support that helps the dentist to maintain that spacing during the light-curing step. The risk that the wand might be spaced too far from the restoration to cause complete curing of the restorative material is thereby avoided. Also avoided is the problem that the end of the wand might be positioned too close to the area of restoration to produce uniform curing of all of the material, or that the end surface 38 of the wand might come into direct contact with such material to mar the surface of the restoration and cause restorative material to cling to wand surface 38 and impair the operation of the light-directing apparatus. The shield also protects the dentist against high-intensity light reflected from dental surfaces, as well as offering some protection for the patient and others should the wand to be moved into and out of position in illuminated condition.

The holder 16 of FIG. 2 comprises a block 50 of metal or substantially opaque plastic material having a spring clip 51 for receiving a portion of the handle 35 of wand 13. A cylindrical cavity or recess 52 is dimensioned to receive the conical shield 15. Since the diameter of the cavity is only slightly greater than that of the shield, light escaping from the cavity, should the wand be illuminated while in the holder, would not reach objectionable levels. The holder may be conveniently mounted by screws 53 to a dental tray or to any other structure within easy reach of the dentist. In the illustration given, the screws 53 are threaded into a clamping plate 54 and a member M of the dental tray assembly is clamped between plate 54 and block 50.

Since the spacer shield 15 is readily detachable from wand 13, and since it is a relatively inexpensive component of the system, sterilization of the shield following use may be considered less effecient and desirable than simply discarding a used shield and, when the wand is again needed, replacing it with a new shield which is most advantageously packaged by the manufacturer and stored by the dentist in sterile condition.

While in the foregoing I have disclosed an embodiment of the invention in considerable detail for purposes of illustration, it will be understood by those skilled in the art that many of these details may be varied without departing from the spirit and scope of the invention.

I claim:

1. An apparatus for use in directing high-intensity light to an operative site for polymerizing a light-sensitive dental restorative material; said apparatus including a light source, a light-directing wand adapted to be hand-held by a user, and means for transmitting light from said source to said wand; wherein the improvement comprises
   spacing means for engaging a tooth and for spacing the light-emitting end of said wand a predetermined distance from the restorative material at an operative site; said spacing means consisting essentially of a frusto-conical shield having a proximal end defining a reduced opening and a tooth-engagable distal end defining an enlarged opening; means at said proximal end for coupling said shield to the light-emitting distal end of said wand; said enlarged opening of said shield having a diameter within the range of about 0.35 to 0.85 inches; said shield having an interior surface sloping from the shield's axis at an angle within the range of about 15° to 35°.

2. The apparatus of claim 1 in which said angle falls within the range of about 20° to 25°.

3. The apparatus of claim 1 in which said diameter of said enlarged opening falls within the range of about 0.40 to 0.65 inches.

4. The apparatus of claim 1 in which said shield has a length between said reduced and enlarged openings falling within the range of about 0.25 to 0.50 inches.

5. The apparatus of claim 1 in which said shield is opaque.

6. The apparatus of claim 5 in which said shield is formed of substantially rigid plastic material.

7. The apparatus of claim 1 in which said means comprises a tubular collar formed integrally with said shield and adapted to receive the distal end portion of said wand.

8. The apparatus of claim 7 in which said tubular sleeve frictionally and detachably receives said distal end portion of said wand.

9. The apparatus of claim 8 in which an internal shoulder is provided at said reduced opening for limiting the extent of insertion of said distal end portion of said wand within said tubular sleeve.

10. The apparatus of claim 1 in which said shield has a light-reflective interior surface.

11. The apparatus of claim 1 in which said enlarged opening of said shield is generally circular.

12. The apparatus of claim 1 in which said apparatus includes a holder for releasably supporting said wand and shield; said holder having a recess for receiving said shield and having spring clip means for releasably gripping and supporting said wand.

13. The apparatus of claim 1 in which said light source is disposed within a light box having a plurality of sockets aligned with said source; said means for transmitting light from said source to said wand comprising a cable having a plug receivable in one of said sockets; and another of said plurality of sockets being adapted to receive the end of a second cable of an illuminating dental instrument, whereby, light may be simultaneously transmitted from said light source to both said wand and said instrument.

14. A spacing shield adapted to be mounted at the light-emitting distal end of a fiber-optic light wand used for photo-curing of polymerizable dental restorative materials, said spacing shield including a frusto-conical portion having an enlarged tooth-engagable distal end with an enlarged opening therein and a reduced proximal end with a reduced opening therein, a tubular sleeve portion formed integrally with said frusto-conical portion and projecting axially from the reduced end thereof, said sleeve portion being adapted to receive and frictionally engage the distal end of a light wand, said enlarged opening of said shield having a diameter within the range of about 0.35 to 0.85 inches, said shield having an interior surface sloping from the axis of the shield at an angle within the range of about 15° to 35°.

15. The spacing shield of claim 14 in which said angle falls within the range of about 20° to 25°.

16. The spacing shield of claim 14 in which said diameter of said enlarged opening falls within the range of about 0.40 to 0.65 inches.

17. The spacing shield of claim 14 in which said shield has a length between said reduced and enlarged openings falling within the range of about 0.25 to 0.50 inches.

18. The spacing shield of claim 14 in which said shield is opaque.

19. The spacing shield of claim 14 in which said shield portion has a light-reflective frusto-conical interior surface.

20. The spacing shield of claim 14 in which an internal shoulder is provided at said reduced opening for engaging the distal end of a wand and for limiting the extent of insertion of said distal end into said tubular sleeve.

* * * * *

UNITED STATES PATENT AND TRADEMARK OFFICE
CERTIFICATE OF CORRECTION

PATENT NO. : 4,445,858
DATED : May 1, 1984
INVENTOR(S) : Clifford C. Johnson

It is certified that error appears in the above—identified patent and that said Letters Patent are hereby corrected as shown below:

On the title page
Assignee should be changed from "American Hospital Supply Corporation" to -- SYBRON CORPORATION --.

Signed and Sealed this

Sixth Day of November 1984

[SEAL]

Attest:

GERALD J. MOSSINGHOFF

Attesting Officer

Commissioner of Patents and Trademarks